United States Patent
Li et al.

(10) Patent No.: US 10,604,740 B2
(45) Date of Patent: Mar. 31, 2020

(54) NUCLEIC ACIDS ENCODING CHIMERIC ANTIGEN RECEPTOR PROTEINS WHICH BIND EPIDERMAL GROWTH FACTOR RECEPTOR AND T LYMPHOCYTE EXPRESSING THE PROTEIN

(71) Applicant: CARSGEN THERAPEUTICS LIMITED, Shanghai (CN)

(72) Inventors: Zonghai Li, Shanghai (CN); Huiping Gao, Shanghai (CN); Hua Jiang, Shanghai (CN); Bizhi Shi, Shanghai (CN)

(73) Assignee: CarsGEN Therapeutics Limited, Shanghai (CN)

( * ) Notice: Subject to any disclaimer, the term of this patent is extended or adjusted under 35 U.S.C. 154(b) by 0 days.

(21) Appl. No.: 15/310,495

(22) PCT Filed: May 14, 2014

(86) PCT No.: PCT/CN2014/077517
§ 371 (c)(1),
(2) Date: Nov. 11, 2016

(87) PCT Pub. No.: WO2015/172339
PCT Pub. Date: Nov. 19, 2015

(65) Prior Publication Data
US 2017/0159025 A1  Jun. 8, 2017

(51) Int. Cl.
| | | |
|---|---|---|
| *C12N 5/16* | (2006.01) | |
| *C12N 7/00* | (2006.01) | |
| *C12N 15/62* | (2006.01) | |
| *C07K 14/71* | (2006.01) | |
| *C07K 14/705* | (2006.01) | |
| *C07K 14/725* | (2006.01) | |

(52) U.S. Cl.
CPC .......... *C12N 5/163* (2013.01); *C07K 14/7051* (2013.01); *C07K 14/70503* (2013.01); *C07K 14/70517* (2013.01); *C07K 14/70521* (2013.01); *C07K 14/71* (2013.01); *C12N 7/00* (2013.01); *C12N 15/62* (2013.01); *C12N 2740/15043* (2013.01)

(58) Field of Classification Search
CPC . C12N 5/163; C12N 5/62; C12N 7/00; C12N 2740/15043
See application file for complete search history.

(56) References Cited

FOREIGN PATENT DOCUMENTS

| | | | |
|---|---|---|---|
| CN | 103382223 A | | 11/2013 |
| CN | 103596981 A | | 2/2014 |
| CN | 104087607 | * | 10/2014 |
| CN | 107058354 | * | 8/2017 |
| EP | 3126006 A1 | | 2/2017 |
| JP | 2010536340 A | | 12/2010 |
| JP | 2014507118 A | | 3/2014 |
| WO | WO-2012138475 A1 | | 10/2012 |
| WO | WO-2013123061 A1 | | 8/2013 |
| WO | WO-2013149526 A1 | | 10/2013 |
| WO | WO-2015172339 A1 | | 11/2015 |

OTHER PUBLICATIONS

Lloyd C, et al. (2009) Protein Engineering, Design and Selection. 22(3):159-168. (doi:10.1093/protein/gzn058).*
International Search Report dated Feb. 17, 2016 corresponding to International Patent Application No. PCT/CN2014/077517, filed on May 14, 2014, 2 pages.
Dotti, et al. Design and Development of Therapies using Chimeric Antigen Receptor-Expressing T cells. Immunol Rev. Jan. 2014; 257(1).
Shen, et al. Chimeric antigen receptor containing ICOS signaling domain mediates specific and efficient antitumor effect of T cells against EGFRvIII expressing glioma. J Hematol Oncol. 2013; 6: 33.
Gan et al. Targeting of a Conformationally Exposed, Tumor-Specific Epitope of EGFR as a Strategy for Cancer Therapy, Cancer Research, 2012, 72(12):2924-2930.
Garretta, et al., Antibodies specifically targeting a locally misfolded region of tumor associated EGFR, PNAS, Mar. 31, 2009 106(13):5082-5087.

* cited by examiner

*Primary Examiner* — Robert S Landsman
(74) *Attorney, Agent, or Firm* — Wilson Sonsini Goodrich & Rosati

(57) ABSTRACT

A nucleic acid for coding a chimeric antigen receptor protein expressed on the surface of a human T lymphocyte. The chimeric antigen receptor protein comprises an extracellular binding domain, a transmembrane domain and an intracellular signal domain that are orderly connected. The extracellular binding domain comprises a single-chain antibody scFv (EGFR) for specific recognition of $287^{th}$ to $302^{nd}$ amino acid epitopes of a human epidermal growth factor receptor (EGFR).

18 Claims, 3 Drawing Sheets
Specification includes a Sequence Listing.

SEQUENCE LISTING

<160> NUMBER OF SEQ ID NOS: 34

<210> SEQ ID NO 1
<211> LENGTH: 1260
<212> TYPE: DNA
<213> ORGANISM: Artificial Sequence
<220> FEATURE:
<223> OTHER INFORMATION: Polynucleotide

<400> SEQUENCE: 1

```
gacatcctga tgacccaatc tccatcctcc atgtctgtat ctctgggaga cacagtcagc      60
atcacttgcc attcaagtca ggacattaac agtaatatag ggtggttgca gcagagacca     120
gggaaatcat ttaagggcct gatctatcat ggaaccaact tggacgatga agttccatca     180
aggttcagtg gcagtggatc tggagccgat tattctctca ccatcagcag cctggaatct     240
gaagattttg cagactatta ctgtgtacag tatgctcagt ttccgtggac gttcggtgga     300
ggcaccaagc tggaaatcaa acgtggtgga ggcggttcag gcggaggtgg ctctggcggt     360
ggcggatcgg ccgatgtgca gcttcaggag tcgggaccta gcctggtgaa accttctcag     420
tctctgtccc tcacctgcac tgtcactggc tactcaatca ccagtgattt tgcctggaac     480
tggatccggc agtttccagg aaacaagctg gagtggatgg gctacataag ttatagtggt     540
aacactaggt acaacccatc tctcaaaagt cgaatctcta tcactcgaga cacatccaag     600
aaccaattct cctgcagtt gaattctgtg actattgagg acacagccac atattactgt     660
gtaacggcgg gacgcgggtt tccttattgg ggccaaggga ctctggtcac tgtctctgca     720
accacgacgc cagcgccgcg accaccaaca ccggcgccca ccatcgcgtc gcagcccctg     780
tccctgcgcc cagaggcgtg ccggccagcg gcggggggcg cagtgcacac gagggggctg     840
gacttcgcct gtgatatcta catctgggcg cccttggccg ggacttgtgg ggtccttctc     900
ctgtcactgg ttatcaccag agtgaagttc agcaggagcg cagacgcccc cgcgtaccag     960
cagggccaga accagctcta taacgagctc aatctaggac gaagagagga gtacgatgtt    1020
ttggacaaga cgtggccg ggaccctgag atgggggaa agccgcagag aaggaagaac    1080
cctcaggaag gcctgtacaa tgaactgcag aaagataaga tggcggaggc ctacagtgag    1140
attgggatga aggcgagcg ccggaggggc aaggggcacg atggccttta ccagggtctc    1200
agtacagcca ccaaggacac ctacgacgcc ttcacatgc aggccctgcc ccctcgctag    1260
```

<210> SEQ ID NO 2
<211> LENGTH: 1527
<212> TYPE: DNA
<213> ORGANISM: Artificial Sequence
<220> FEATURE:
<223> OTHER INFORMATION: Polynucleotide

<400> SEQUENCE: 2

```
gccgatgtgc agcttcagga gtcgggacct agcctggtga aaccttctca gtctctgtcc      60
ctcacctgca ctgtcactgg ctactcaatc accagtgatt ttgcctggaa ctggatccgg     120
cagtttccag gaaacaagct ggagtggatg gctacataa gttatagtgg taacactagg     180
tacaacccat ctctcaaaag tcgaatctct atcactcgag acacatccaa gaaccaattc     240
tcctgcagt tgaattctgt gactattgag acacagcca catattactg tgtaacggcg     300
gacgcgggt tccttattg gggccaaggg actctggtca ctgtctctgc aggtggaggc     360
ggttcaggcg gaggtggctc tggcggtggc ggatcggaca tcctgatgac ccaatctcca     420
tcctccatgt ctgtatctct gggagacaca gtcagcatca cttgccattc aagtcaggac     480
attaacagta atatagggtg gttgcagcag agaccaggga atcatttaa gggcctgatc     540
tatcatggaa ccaacttgga cgatgaagtt ccatcaaggt tcagtggcag tggatctgga     600
gccgattatt ctctcaccat cagcagcctg aatctgaag attttgcaga ctattactgt     660
gtacagtatg ctcagtttcc gtggacgttc ggtggaggca ccaagctgga aatcaaacgt     720
```

| | |
|---|---|
| accacgacgc cagcgccgcg accaccaaca ccggcgccca ccatcgcgtc gcagcccctg | 780 |
| tccctgcgcc cagaggcgtg ccggccagcg gcggggggcg cagtgcacac gagggggctg | 840 |
| gacttcgcct gtgattttg ggtgctggtg gtggttggtg gagtcctggc ttgctatagc | 900 |
| ttgctagtaa cagtggcctt tattattttc tgggtgagga gtaagaggag caggctcctg | 960 |
| cacagtgact acatgaacat gactccccgc cgccccgggc caacccgcaa gcattaccag | 1020 |
| ccctatgccc caccacgcga cttcgcagcc tatcgctcca aacggggcag aaagaaactc | 1080 |
| ctgtatatat tcaaacaacc atttatgaga ccagtacaaa ctactcaaga ggaagatggc | 1140 |
| tgtagctgcc gatttccaga agaagaagaa ggaggatgtg aactgagagt gaagttcagc | 1200 |
| aggagcgcag acgcccccgc gtaccagcag ggccagaacc agctctataa cgagctcaat | 1260 |
| ctaggacgaa gagaggagta cgatgttttg gacaagagac gtggccggga ccctgagatg | 1320 |
| gggggaaagc cgcagagaag gaagaaccct caggaaggcc tgtacaatga actgcagaaa | 1380 |
| gataagatgg cggaggccta cagtgagatt gggatgaaag cgagcgccg gagggcaag | 1440 |
| gggcacgatg gcctttacca gggtctcagt acagccacca aggacaccta cgacgccctt | 1500 |
| cacatgcagg ccctgccccc tcgctag | 1527 |

<210> SEQ ID NO 3
<211> LENGTH: 1260
<212> TYPE: DNA
<213> ORGANISM: Artificial Sequence
<220> FEATURE:
<223> OTHER INFORMATION: Polynucleotide

<400> SEQUENCE: 3

| | |
|---|---|
| gatattcaga tgacccagag cccgagcagc ctgagcgcga gcgtgggcga ccgtgtgacc | 60 |
| attacctgcc atgcgagcca ggatattaac agcaacattg gctggctgca gcagaaaccg | 120 |
| ggcaaagcgt ttaaaggcct gatttatcat ggcaaaaacc tggaagatgg cgtgccgagc | 180 |
| cgttttagcg gcagcggcag cggcaccgat tttacccctga ccattagcag cctgcagccg | 240 |
| gaagattttg cgacctatta ttgcgttcag tacgcccagt tcccatatac atttggccag | 300 |
| ggcaccaaag tggaaattaa acgttcaggt ggaggcggtt caggcggagg tggctctggc | 360 |
| ggtggcggat cggatgtgca gctggtggaa agcggcggcg gcctggtgca gccgggcggc | 420 |
| agcctgcgtc tgagctgcgc ggtgagcggc tatagcatta ccagcgatta tgcgtggaac | 480 |
| tggattcgtc aggcgccggg caaaggcctg gaatggctgg gctatattag ctatcgcggc | 540 |
| cgcaccagct ataacccgag cctgaaaagc cgtattagca ttacccgtga taacagcaaa | 600 |
| aacacctttt tcctgcagct gaacagcctg cgtgcggaag ataccgcggt gtattattgc | 660 |
| gcgcgcctgg gacgcggctt ccgctactgg ggccagggca ccctggtgac cgtgagcagc | 720 |
| accacgacgc cagcgccgcg accaccaaca ccggcgccca ccatcgcgtc gcagcccctg | 780 |
| tccctgcgcc cagaggcgtg ccggccagcg gcggggggcg cagtgcacac gagggggctg | 840 |
| gacttcgcct gtgatatcta catctgggcg cccttggccg ggacttgtgg ggtccttctc | 900 |
| ctgtcactgg ttatcaccag agtgaagttc agcaggagcg cagacgcccc cgcgtaccag | 960 |
| cagggccaga accagctcta taacgagctc aatctaggac gaagagagga gtacgatgtt | 1020 |
| ttggacaaga gacgtggccg ggaccctgag atgggggggaa agccgcagag aaggaagaac | 1080 |
| cctcaggaag gcctgtacaa tgaactgcag aaagataaga tggcggaggc ctacagtgag | 1140 |
| attgggatga aggcgagcg ccggaggggc aaggggcacg atggccttta ccagggtctc | 1200 |
| agtacagccca ccaaggacac ctacgacgcc cttcacatgc aggccctgcc cctcgctag | 1260 |

<210> SEQ ID NO 4
<211> LENGTH: 1527
<212> TYPE: DNA
<213> ORGANISM: Artificial Sequence
<220> FEATURE:
<223> OTHER INFORMATION: Polynucleotide

<400> SEQUENCE: 4

```
gatattcaga tgacccagag cccgagcagc ctgagcgcga gcgtgggcga ccgtgtgacc      60
attacctgcc atgcgagcca ggatattaac agcaacattg ctggctgca gcagaaaccg     120
ggcaaagcgt ttaaaggcct gatttatcat ggcaaaaacc tggaagatgg cgtgccgagc     180
cgttttagcg gcagcggcag cggcaccgat tttaccctga ccattagcag cctgcagccg     240
gaagattttg cgacctatta ttgcgttcag tacgcccagt ccccatatac atttggccag     300
ggcaccaaag tggaaattaa acgttcaggt ggaggcggtt caggcggagg tggctctggc     360
ggtggcggat cggatgtgca gctggtggaa agcggcggcg gcctggtgca gccgggcggc     420
agcctgcgtc tgagctgcgc ggtgagcggc tatagcatta ccagcgatta tgcgtggaac     480
tggattcgtc aggcgccggg caaaggcctg aatggctgg gctatattag ctatcgcggc     540
cgcaccagct ataacccgag cctgaaaagc cgtattagca ttacccgtga taacagcaaa     600
aacaccttt tcctgcagct gaacagcctg cgtgcgaag ataccgcggt gtattattgc       660
gcgcgcctgg gacgcggctt ccgctactgg ggccagggca cctggtgac cgtgagcagc     720
accacgacgc cagcgccgcg accaccaaca ccggcgccca ccatcgcgtc gcagcccctg     780
tccctgcgcc agaggcgtg ccggccagcg gcggggggcg cagtgcacac gagggggctg      840
gacttcgcct gtgatttttg ggtgctggtg gtggttggtg gagtcctggc ttgctatagc     900
ttgctagtaa cagtggcctt tattattttc tgggtgagga gtaagaggag caggctcctg     960
cacagtgact acatgaacat gactccccgc cgccccgggc aacccgcaa gcattaccag     1020
ccctatgccc caccacgcga cttcgcagcc tatcgctcca acggggcag aaagaaactc     1080
ctgtatatat tcaaacaacc atttatgaga ccagtacaaa ctactcaaga ggaagatggc     1140
tgtagctgcc gatttccaga agaagaagaa ggaggatgtg aactgagagt gaagttcagc     1200
aggagcgcag acgcccccgc gtaccagcag ggccagaacc agctctataa cgagctcaat     1260
ctaggacgaa gagaggagta cgatgttttg gacaagagac gtggccggga ccctgagatg     1320
gggggaaagc gcagagaag gaagaaccct caggaaggcc tgtacaatga actgcagaaa     1380
gataagatgg cggaggccta cagtgagatt gggatgaaag cgagcgccg gaggggcaag     1440
gggcacgatg gcctttacca gggtctcagt acagccacca aggacaccta cgacgccctt     1500
cacatgcagg ccctgccccc tcgctag                                        1527
```

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5

```
gacatcctga tgacccaatc tccatcctc                                        29
```

<210> SEQ ID NO 6
<211> LENGTH: 28
<212> TYPE: DNA

```
<213> ORGANISM: Artificial Sequence
<220> FEATURE:
<223> OTHER INFORMATION: Primer

<400> SEQUENCE: 6
tgcagagaca gtgaccagag tcccttgg                                       28

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
gatattcaga tgacccagag cccg                                           24

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gctgctcacg gtcaccaggg tg                                             22

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
cactgtctct gcaaccacga cgccagcg                                       28

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ggtgataacc agtgacagga g                                              21

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
cactgtctct gcaaccacga cgccagcg                                       28

<210> SEQ ID NO 12
<211> LENGTH: 62
<212> TYPE: DNA
<213> ORGANISM: Artificial Sequence
<220> FEATURE:
<223> OTHER INFORMATION: Primer

<400> SEQUENCE: 12
gaggtcgacc tacgcggggg cgtctgcgct cctgctgaac ttcactctgg tgataaccag    60
``` tg                                                              62

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
ttttgggtgc tggtggtggt tgg                                       23

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
gctgaacttc actctggagc gataggctgc gaag                           34

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
aaacggggca gaaagaaact c                                         21

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
cagttcacat cctccttc                                             18

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
cactggttat caccagagtg aagttcagca ggagc                          35

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
cgaggtcgac ctagcgaggg ggcagggcct gcatg                          35

<210> SEQ ID NO 19
<211> LENGTH: 18
<212> TYPE: DNA

```
<213> ORGANISM: Artificial Sequence
<220> FEATURE:
<223> OTHER INFORMATION: Primer

<400> SEQUENCE: 19
accacgacgc cagcgccg                                                       18

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
cacccagaaa ataataaag                                                      19

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
agagtgaagt tcagcaggag cgcag                                               25

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
cactgtctct gcaaccacga cgccagcg                                            28

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
cactgtctct gcaaccacga cgccagcg                                            28

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
accacgacgc cagcgccg                                                       18

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
attcaaagtc tgtttcacgc tactagctag tccg                                     34
```

<210> SEQ ID NO 26
<211> LENGTH: 57
<212> TYPE: DNA
<213> ORGANISM: Artificial Sequence
<220> FEATURE:
<223> OTHER INFORMATION: Primer

<400> SEQUENCE: 26
gtgaaacaga ctttgaattt tgaccttctg aagttggcag gagacgttga gtccaac            57

<210> SEQ ID NO 27
<211> LENGTH: 59
<212> TYPE: DNA
<213> ORGANISM: Artificial Sequence
<220> FEATURE:
<223> OTHER INFORMATION: Primer

<400> SEQUENCE: 27
agcggcagga gcaaggcggt cactggtaag gccatgggcc cagggttgga ctcaacgtc         59

<210> SEQ ID NO 28
<211> LENGTH: 59
<212> TYPE: DNA
<213> ORGANISM: Artificial Sequence
<220> FEATURE:
<223> OTHER INFORMATION: Primer

<400> SEQUENCE: 28
ctcctgccgc tggccttgct gctccacgcc gccaggccgg acatcctgat gacccaatc         59

<210> SEQ ID NO 29
<211> LENGTH: 52
<212> TYPE: DNA
<213> ORGANISM: Artificial Sequence
<220> FEATURE:
<223> OTHER INFORMATION: Primer

<400> SEQUENCE: 29
cttacgcgtc ctagcgctac cggtcgccac catggtgagc aagggcgagg ag               52

<210> SEQ ID NO 30
<211> LENGTH: 37
<212> TYPE: DNA
<213> ORGANISM: Artificial Sequence
<220> FEATURE:
<223> OTHER INFORMATION: Primer

<400> SEQUENCE: 30
gctactagct agtccggact tgtacagctc gtccatg                                 37

<210> SEQ ID NO 31
<211> LENGTH: 419
<212> TYPE: PRT
<213> ORGANISM: Artificial Sequence
<220> FEATURE:
<223> OTHER INFORMATION: Polypeptide

<400> SEQUENCE: 31

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

```
Tyr His Gly Thr Asn Leu Asp Asp Glu Val Pro Ser Arg Phe Ser Gly
         50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Trp
                 85                  90                  95

Thr Phe Gly Gly Gly Thr Lys Leu Glu Ile Lys Arg Gly Gly Gly Gly
                100                 105                 110

Ser Gly Gly Gly Gly Ser Gly Gly Gly Ser Ala Asp Val Gln Leu
                115                 120                 125

Gln Glu Ser Gly Pro Ser Leu Val Lys Pro Ser Gln Ser Leu Ser Leu
130                 135                 140

Thr Cys Thr Val Thr Gly Tyr Ser Ile Thr Ser Asp Phe Ala Trp Asn
145                 150                 155                 160

Trp Ile Arg Gln Phe Pro Gly Asn Lys Leu Glu Trp Met Gly Tyr Ile
                165                 170                 175

Ser Tyr Ser Gly Asn Thr Arg Tyr Asn Pro Ser Leu Lys Ser Arg Ile
                180                 185                 190

Ser Ile Thr Arg Asp Thr Ser Lys Asn Gln Phe Phe Leu Gln Leu Asn
                195                 200                 205

Ser Val Thr Ile Glu Asp Thr Ala Thr Tyr Tyr Cys Val Thr Ala Gly
210                 215                 220

Arg Gly Phe Pro Tyr Trp Gly Gln Gly Thr Leu Val Thr Val Ser Ala
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
                260                 265                 270

Gly Ala Val His Thr Arg Gly Leu Asp Phe Ala Cys Asp Ile Tyr Ile
                275                 280                 285

Trp Ala Pro Leu Ala Gly Thr Cys Gly Val Leu Leu Leu Ser Leu Val
                290                 295                 300

Ile Thr Arg Val Lys Phe Ser Arg Ser Ala Asp Ala Pro Ala Tyr Gln
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
                340                 345                 350

Gly Lys Pro Gln Arg Arg Lys Asn Pro Gln Glu Gly Leu Tyr Asn Glu
                355                 360                 365

Leu Gln Lys Asp Lys Met Ala Glu Ala Tyr Ser Glu Ile Gly Met Lys
370                 375                 380

Gly Glu Arg Arg Arg Gly Lys Gly His Asp Gly Leu Tyr Gln Gly Leu
385                 390                 395                 400

Ser Thr Ala Thr Lys Asp Thr Tyr Asp Ala Leu His Met Gln Ala Leu
                405                 410                 415

Pro Pro Arg

<210> SEQ ID NO 32
<211> LENGTH: 508
<212> TYPE: PRT
<213> ORGANISM: Artificial Sequence
<220> FEATURE:
<223> OTHER INFORMATION: Polypeptide
```

<400> SEQUENCE: 32

```
Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Gly Gly Gly Gly
                100                 105                 110

Ser Gly Gly Gly Gly Ser Gly Gly Gly Ser Ala Asp Val Gln Leu
            115                 120                 125

Gln Glu Ser Gly Pro Ser Leu Val Lys Pro Ser Gln Ser Leu Ser Leu
130                 135                 140

Thr Cys Thr Val Thr Gly Tyr Ser Ile Thr Ser Asp Phe Ala Trp Asn
145                 150                 155                 160

Trp Ile Arg Gln Phe Pro Gly Asn Lys Leu Glu Trp Met Gly Tyr Ile
                165                 170                 175

Ser Tyr Ser Gly Asn Thr Arg Tyr Asn Pro Ser Leu Lys Ser Arg Ile
            180                 185                 190

Ser Ile Thr Arg Asp Thr Ser Lys Asn Gln Phe Phe Leu Gln Leu Asn
        195                 200                 205

Ser Val Thr Ile Glu Asp Thr Ala Thr Tyr Tyr Cys Val Thr Ala Gly
210                 215                 220

Arg Gly Phe Pro Tyr Trp Gly Gln Gly Thr Leu Val Thr Val Ser Ala
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Phe Trp Val
        275                 280                 285

Leu Val Val Val Gly Gly Val Leu Ala Cys Tyr Ser Leu Leu Val Thr
290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser Lys Arg Gly Arg Lys Lys Leu Leu Tyr Ile Phe Lys Gln Pro Phe
        355                 360                 365

Met Arg Pro Val Gln Thr Thr Gln Glu Glu Asp Gly Cys Ser Cys Arg
370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Gln Gln Gly Gln Asn Gln Leu Tyr
```

```
                    405                 410                 415
Asn Glu Leu Asn Leu Gly Arg Arg Glu Glu Tyr Asp Val Leu Asp Lys
                420                 425                 430

Arg Arg Gly Arg Asp Pro Glu Met Gly Gly Lys Pro Gln Arg Arg Lys
            435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 33
<211> LENGTH: 419
<212> TYPE: PRT
<213> ORGANISM: Artificial Sequence
<220> FEATURE:
<223> OTHER INFORMATION: Polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Ser Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Ala Gln Phe Pro Tyr
                85                  90                  95

Thr Phe Gly Gln Gly Thr Lys Val Glu Ile Lys Arg Ser Gly Gly Gly
            100                 105                 110

Gly Ser Gly Gly Gly Gly Ser Gly Gly Gly Ser Asp Val Gln Leu
        115                 120                 125

Val Glu Ser Gly Gly Gly Leu Val Gln Pro Gly Gly Ser Leu Arg Leu
    130                 135                 140

Ser Cys Ala Val Ser Gly Tyr Ser Ile Thr Ser Asp Tyr Ala Trp Asn
145                 150                 155                 160

Trp Ile Arg Gln Ala Pro Gly Lys Gly Leu Glu Trp Leu Gly Tyr Ile
                165                 170                 175

Ser Tyr Arg Gly Arg Thr Ser Tyr Asn Pro Ser Leu Lys Ser Arg Ile
            180                 185                 190

Ser Ile Thr Arg Asp Asn Ser Lys Asn Thr Phe Phe Leu Gln Leu Asn
        195                 200                 205

Ser Leu Arg Ala Glu Asp Thr Ala Val Tyr Tyr Cys Ala Arg Leu Gly
    210                 215                 220

Arg Gly Phe Arg Tyr Trp Gly Gln Gly Thr Leu Val Thr Val Ser Ser
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
```

```
                    260                 265                 270
Gly Ala Val His Thr Arg Gly Leu Asp Phe Ala Cys Asp Ile Tyr Ile
            275                 280                 285

Trp Ala Pro Leu Ala Gly Thr Cys Gly Val Leu Leu Leu Ser Leu Val
        290                 295                 300

Ile Thr Arg Val Lys Phe Ser Arg Ser Ala Asp Ala Pro Ala Tyr Gln
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Gln Arg Arg Lys Asn Pro Gln Glu Gly Leu Tyr Asn Glu
        355                 360                 365

Leu Gln Lys Asp Lys Met Ala Glu Ala Tyr Ser Glu Ile Gly Met Lys
        370                 375                 380

Gly Glu Arg Arg Arg Gly Lys Gly His Asp Gly Leu Tyr Gln Gly Leu
385                 390                 395                 400

Ser Thr Ala Thr Lys Asp Thr Tyr Asp Ala Leu His Met Gln Ala Leu
                405                 410                 415

Pro Pro Arg

<210> SEQ ID NO 34
<211> LENGTH: 508
<212> TYPE: PRT
<213> ORGANISM: Artificial Sequence
<220> FEATURE:
<223> OTHER INFORMATION: Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Ser Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Ala Gln Phe Pro Tyr
                85                  90                  95

Thr Phe Gly Gln Gly Thr Lys Val Glu Ile Lys Arg Ser Gly Gly Gly
            100                 105                 110

Gly Ser Gly Gly Gly Gly Ser Gly Gly Gly Ser Asp Val Gln Leu
        115                 120                 125

Val Glu Ser Gly Gly Gly Leu Val Gln Pro Gly Gly Ser Leu Arg Leu
    130                 135                 140

Ser Cys Ala Val Ser Gly Tyr Ser Ile Thr Ser Asp Tyr Ala Trp Asn
145                 150                 155                 160

Trp Ile Arg Gln Ala Pro Gly Lys Gly Leu Glu Trp Leu Gly Tyr Ile
                165                 170                 175

Ser Tyr Arg Gly Arg Thr Ser Tyr Asn Pro Ser Leu Lys Ser Arg Ile
            180                 185                 190

Ser Ile Thr Arg Asp Asn Ser Lys Asn Thr Phe Phe Leu Gln Leu Asn
        195                 200                 205
```

Ser Leu Arg Ala Glu Asp Thr Ala Val Tyr Tyr Cys Ala Arg Leu Gly
    210                 215                 220

Arg Gly Phe Arg Tyr Trp Gly Gln Gly Thr Leu Val Thr Val Ser Ser
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Phe Trp Val
            275                 280                 285

Leu Val Val Val Gly Gly Val Leu Ala Cys Tyr Ser Leu Leu Val Thr
            290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
                340                 345                 350

Ser Lys Arg Gly Arg Lys Lys Leu Leu Tyr Ile Phe Lys Gln Pro Phe
                355                 360                 365

Met Arg Pro Val Gln Thr Thr Gln Glu Glu Asp Gly Cys Ser Cys Arg
        370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Gln Arg Arg Lys
            435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

NUCLEIC ACIDS ENCODING CHIMERIC ANTIGEN RECEPTOR PROTEINS WHICH BIND EPIDERMAL GROWTH FACTOR RECEPTOR AND T LYMPHOCYTE EXPRESSING THE PROTEIN

TECHNICAL FIELD

The present invention relates to the treatment of tumor by cellular therapy, and more particularly, to the treatment of tumor of epithelial origin with expression of EGFRvIII or high expression of EGFR by transgenic T lymphocyte therapy.

REFERENCE TO A "SEQUENCE LISTING,"

The Sequence_Listing.txt, created on Nov. 10, 2016, 28,734 bytes, machine format IBM-PC, MS-Windows operating system, is hereby incorporated by reference in its entirety for all purposes.

BACKGROUND

The Epidermal Growth Factor receptor (EGFR) is a transmembrane glycoprotein, the molecular weight of which is 170 KD. It is an expression product of oncogene C-erbB-1 (HER-1), and widely distributed on cell membrane of human tissues [Alan Wells. Molecules in focus EGF receptor. Int J Biochem Cell Biol, 1999, 31: 637-643]. It is over-expressed and (or) mutated in most tumors (For example, non-small cell lung cancer, bladder cancer, ovarian cancer, breast cancer, head and neck squamous cell carcinoma, glioblastoma, pancreatic cancer, esophageal cancer, gastric cancer, prostate cancer, etc.), and is closely related to the occurrence and development of tumor, malignant transformation, metastasis and prognosis [Jose B Why the epidermal growth factor receptor? The rational for cancer therapy [J] oncologist, 2002, 7 (4): 2-8]. Therefore, EGFR is an important target for tumor treatment. In addition, studies have shown that EGFR 287-302 epitope is only exposed in tumors expressing EGFRvIII or over-expressing EGFR, while concealed in normal tissues [Gan H K, et. Al Targeting of a conformationally exposed, tumor-specific epitope of EGFR as a strategy for cancer therapy. Cancer Res, 2012, 72 (12): 2924-2930]. It is suggested that EGFR 287-302 epitope is an ideal site for targeting EGFR-relevant tumor therapy.

Antibodies against EGFR287-302 epitope have been developed, exhibiting good tumor-specific killing effects. However, antibody therapy is limited by the in vivo half-life of antibody in the blood circulation. Generally, the half-life is not more than 23 days. Therefore, sustained administration, and/or increase in the dose is necessary for the antibody therapy of tumor, which results in the increase of cost for patients, and in some cases even results in the termination of treatment. Moreover, the therapeutic antibody, as a heterologous protein, may also be of the risk of producing allergic reactions and neutralizing anti-antibody against the therapeutic antibodies and in vivo.

More and more attention is paid to T lymphocytes in the tumor immune response. Certain effects are achieved by T lymphocyte-based adoptive immunotherapy in some tumors, and such immunotherapy can overcome the above drawbacks of antibody treatment. However, in most tumors, the efficacy is still unsatisfactory [Grupp S A, et. al. Adoptive cellular therapy. Curr Top Microbiol Immunol. 2011, 344: 149-72]. In recent years, according to the discovery that the specificity of cytotoxic T lymphocytes for recognizing target cells depends on T cell receptor (TCR), scFv of the antibody against tumor cell-associated antigen is fused with intracellular signal activation motifs, such as CD3ζ or FcεRIγ, of T cell receptor to form chimeric antigen receptor (CAR), which is genetically modified on the surface of T cell surface by certain means, such as lentivirus infection. Such CAR T cells are capable of selectively redirecting T lymphocytes to tumor cells and specifically killing tumor cells in major histocompatibility complex (MHC) and non-limiting manner. CAR T cell is a new immunotherapeutic strategy in the field of tumor immunotherapy [Schmitz M, et. al. Chimeric antigen receptor-engineered T cells for immunotherapy of Cancer. J Biomed Biotechnol, 2010, doi:10.1155/2010/956304.]

Chimeric antigen receptor comprises extracellular binding domain, transmembrane domain and intracellular signal domain. Generally, extracellular domain comprises scFv capable of recognizing tumor-associated antigen, transmembrane domain is that of molecules, such as CD8, CD28, and immunoreceptor tyrosine-based activation motif (ITAM) such as CD3ζ (i.e., CD3 zeta, abbreviated as Z) or FcsRIy and intracellular signal domain of co-stimulating signal molecule, such as CD28, CD137, CD134 are used in intracellular signal domain.

The first generation of CAR T cells only comprises ITAM in intracellular signal domain, wherein each part of chimeric antigen receptor is connected as follows: scFv-TM-CD3ζ. This kind of CAR T cells can stimulate anti-tumor cytotoxic effects, however the secretion of cytokine is relatively law, and long-lasting anti-tumor effects can not be stimulated in the body [Zhang T. et. al. Chimeric NKG2D-modified T cells inhibit systemic T-cell lymphoma growth in a manner involving multiple cytokines and cytotoxic pathways, Cancer Res 2007, 67(22): 11029-11036].

In the second generation CAR T cells subsequently developed, intracellular signal domain of CD28 or CD137 (also known as 4-1BB) was added, wherein each part of chimeric antigen receptor is connected as follows: scFv-TM-CD28-ITAM or scFv-TM-/CD137-ITAM. Co-stimulating effects of B7/CD28 or 4-1BBL/CD137 occurred in intracellular signal domain lead to the sustained proliferation of T cells, and improve the level of cytokines, such as IL-2 and IFN-γ secreted by T cells, when improving the survival and anti-tumor effects of CAR T in vivo [Dotti G et. al. CD28 costimulation improves expansion and persistence of chimeric antigen receptor modified T cells in lymphoma patients. J Clin Invest, 2011, 121(5):1822-1826.].

In recent years, the third-generation of CAR T cells was developed, wherein each part of chimeric antigen receptor is connected as follows: scFv-TM-CD28-CD137-ITAM or scFv-TM-CD28-CD134-ITAM, thereby further improving the survival and anti-tumor effects of CAR T in vivo [Carpenito C., et al. Control of large established tumor xenografts with genetically retargeted human T cells containing CD28 and CD137 domains. PNAS, 2009, 106(9): 3360-3365].

Despite CAR T cells have an attractive prospect in tumor immunotherapy, but there are also some potential risks to be considered. For example, because some normal tissues can express specific antigens in a low level which can be recognized by CAR, CAR T cells may damage the normal tissues which express the corresponding antigen. The first case of clinically applied adoptive therapy of CAR T cells related to the antigen, carbonic anhydrase IX (CAIX) expressed on tumor cells of patients with renal cell carcinoma, which is also the first reported case about off-target effects of CAR-containing cells. After infused with CAR T cells for several times, 2-4 grade of hepatotoxicity occurs in patients. The reason is that epithelial cells of bile duct express CAIX in low level. And original clinical trial was interrupted while any evaluation on the efficacy of patients was excluded. [Stoter G et al. Treatment of metastatic renal cell carcinoma with autologous T-lymphocytes genetically retargeted against carbonic anhydrase IX: first clinical experience. J clin oncol, 2006, 24(13): e20-e22.; Ngo M C., et al. Ex vivo gene transfer for improved adoptive immunotherapy of cancer. Human Molecular Genetics, 2011, R1-R7]. Additionally, excessive co-stimulating signals in CAR will reduce the threshold for the activation of effector cells, so that the gene-modified T cells with a low level of antigen or without antigen triggering conditions may also be activated, thereby resulting in the release of a large number of cytokines and leading the so-called "cytokine storm". Such signal leakage will result in off-target cytotoxicity, thereby producing non-specific damage to tissues. For example, in the clinic process of treating an advanced colorectal cancer patient with liver and lung metastases by using the third-generation of CAR targeting Her2, so-called "cytokine storm" triggered by the low expression of Her2 in normal lung tissue resulted in sudden death of the patient [Morgan R A., et al. Report of a serious adverse event following the administration of T cells transduced with a chimeric antigen receptor recognizing Erbb2. Molecular Therapy, 2010, 18 (4): 843-851].

Therefore, there is a strong demand in the art to the tumor therapy using CAR T lymphocytes for overcome the above mentioned drawbacks.

SUMMARY

In the first aspect, the present invention relates to a nucleic acid encoding a chimeric antigen receptor protein expressed on the surface of T cells. The chimeric antigen receptor protein comprises sequentially-connected extracellular binding domain, transmembrane domain and intracellular signal domain, wherein the extracellular binding domain comprises a single-chain antibody scFv for the specific recognition of $287^{th}$ to $302^{th}$ amino acid (EGFR287-302) epitope of human epidermal growth factor receptor (EGFR). The extracellular binding domain of the chimeric antigen receptor protein is connected to the transmembrane domain of CD8 or CD28 through CD8 hinge region, and the intracellular signal domain is connected immediately after the transmembrane domain. The polynucleotides of the present invention may be in a form of DNA or RNA. The form of DNA includes cDNA, genomic DNA, or synthetic DNA. DNA may be single-stranded or double-stranded. DNA may be a coding or non-coding strand. The nucleic acid codons of the present invention encoding the amino acid sequence of a chimeric antigen receptor protein may be degenerate, that is, various degenerate nucleic acid sequences encoding the same amino acid sequence are encompassed within the scope of the invention. Degenerate nucleic acid codons encoding corresponding amino acids are well known in the art. The present invention also relates to variants of the above polynucleotides, which encode polypeptides having the same amino acid sequence as the present invention or fragments, analogs and derivatives of the polypeptides. Such variants of polynucleotides may be naturally occurring allelic variants or non-naturally occurring variants. Such nucleotide variants include substitution variants, deletion variants, and insertion variants. As is known in the art, an allelic variant is an alternative form of a polynucleotide, which can be a substitution, deletion or insertion of one or more nucleotides while won't substantially change the function of the encoded polypeptide.

The present invention also relates to polynucleotides that hybridize to the above described sequences and have at least 50%, preferably at least 70%, more preferably at least 80%, most preferably at least 90%, or at least 95% identity between sequences. In particular, the present invention relates to polynucleotides which hybridise with the polynucleotides of the invention under stringent conditions. In the present invention, "stringent condition" means: (1) hybridization and elution at lower ionic strength and higher temperature, such as 0.2×SSC, 0.1% SDS, 60 C; or (2) addition of a denaturant when hybridizing, such as 50% (v/v) formamide, 0.1% fetal calf serum/0.1% Ficoll, 42° C.; or (3) hybridization occurs only under the condition that there is at least 90% or higher, more preferably at least 95% or higher identity between two sequences. And the hybridizable polynucleotide encodes a polypeptide which has the same biological function and activity as the mature polypeptide of SEQ ID NO: 2.

Monoclonal antibodies that specifically recognize the amino acid epitope at positions 287 to 302 of human epidermal growth factor receptor EGFR have been disclosed in CN 102405235 and CN 101602808B, and other monoclonal antibodies specifically recognizing the epitope which are known and will be known can also be used to prepare single-chain antibody in chimeric antigen receptor protein encoded by the nucleic acid of the invention. Single-chain antibody can be prepared by genetic engineering methods or chemical synthesis methods according to the sequences disclosed in the above-mentioned documents. As used herein, the term "single chain antibody (scFv) fragment" refers to an antibody fragment which is a recombinant protein comprising a heavy chain variable region (VH) linked to a light chain variable region (VL) by a linker, and the linker associates the two domains to form an antigen-binding site. Generally, scFv is ⅙ of a complete antibody in size. A single chain antibody is preferably one amino acid chain sequence encoded by one nucleotide chain. Single chain antibodies used in the present invention may be further modified by routine techniques known in the art, such as deletion, insertion, substitution, addition of amino acid, and/or recombination and/or other modification methods, and such techniques can be used alone or in combination. Methods for introducing such modification in the DNA sequences according to the amino acid sequence of an antibody are well known to those skilled in the art; see, for example Sambrook, "Molecular Cloning: A Laboratory Manual", Cold Spring Harbor Laboratory (1989) N.Y. The modification is preferably carried out at the nucleic acid level. The single-chain antibody said above may further include thereof. Methods for preparing the single-chain antibody derivatives includes, but not limited to, a method for the preparation of chimeric antibody described in WO 89/09622, a method for the preparation of humanized antibody described in EP-A10239400 and WO90/07861, a method described in WO91/10741, WO94/02602 and WO96/33735 for the preparation of heterogeneous antibody, such as human antibody in a mouse. The term "specific recognition" used in the present invention means that the bispecific antibody of the invention does not or substantially does not cross-react with any polypeptide other than the target antigen. The degree of specificity can be determined by immunological techniques including, but not limited to, immunoblotting, immunoaffinity chromatography, flow cytometry, and the like. In the present invention, specific recognition is preferably determined by flow cytometry, and in particular, the criteria for specific recognition can be determined by a skilled person in light of the common knowledge in the art.

Transmembrane domain can be selected from the transmembrane domain of a protein such as CD8 or CD28. CD8 or CD28 is a natural marker on the surface of T cells. Human CD8 protein is a heterodimer consisting of αβ or γδ chains. In one embodiment of the present invention, transmembrane domain is selected from the transmembrane domain of CD8a or CD28. In addition, CD8a hinge region is a flexible region, so that the transmembrane domain and hinge region of CD8 or CD28 can be used to link the target recognition domain scFv and intracellular signal domain of chimeric antigen receptor CAR.

Intracellular signal domain can be selected from the intracellular signal domain of CD3, FcεRIγ, CD28, CD137, CD134 proteins, and combinations thereof. CD3 molecule consists of five subunits, in which CD3 subunit (also known as CD3 zeta, abbreviated as Z) contains three ITAM motifs, which is an important signal transduction region in TCR-CD3 complex. CD3δZ is a mutated CD3ζ sequence without ITAM motif, and is generally used to construct a negative control in the practice of the present invention. FcεRIγ is mainly distributed on the surface of mast cells and basophils, which contains an ITAM motif and is similar to CD3ζ in structure, distribution and function. In addition, CD28, CD137, and CD134 are co-stimulatory signal molecules, and after binding to the respective ligands, co-stimulatory effect of the intracellular signal region of these molecules results in the continuous proliferation of T cells and increases the level of IL-2 and IFN-γ secreted by T cells, while improving the survival and anti-tumor effect of CAR T cells in vivo.

The chimeric antigen receptor protein encoded by the nucleic acid of the present invention may comprise sequentially-linked extracellular binding domain, transmembrane domain and intracellular signal domain, for example a chimeric antigen receptor protein selected from the following group:

scFv(EGFR)-CD8-CD3ζ,
scFv(EGFR)-CD8-CD137-CD3ζ,
scFv(EGFR)-CD28-CD28-CD3ζ,
scFv(EGFR)-CD28-CD28-CD137-CD3ζ, or combinations thereof, wherein in the chimeric antigen receptor protein, the first CD28 represents transmembrane domain, and the second CD28 represents intracellular signal domain of the protein.

In one embodiment of the present invention, a nucleic acid of the present invention has a sequence of SEQ ID NOs: 1-4. In another embodiment of the present invention, a nucleic acid of the present invention is a nucleic acid encoding a chimeric antigen receptor protein of one of SEQ ID NOs: 31-34.

The second aspect of the present invention includes a vector comprising the nucleic acid encoding a chimeric antigen receptor protein expressed on the surface of T cells. In a specific embodiment, the vector used in the present invention is a lentiviral plasmid vector pPWT-eGFP. The plasmid belongs to the third-generation of self-inactivating lentiviral vector system. The system consists of three plasmids, that is, packaging plasmid psPAX2 encoding Gag/Pol protein, Rev protein; envelope plasmid PMD2.G encoding VSV-G protein; and blank vector pPWT-eGFP, which can be used to introduce a nucleic acid sequence of interest through recombination, i.e. CAR-encoding nucleic acid sequence. In the blank vector pPT-eGFP (the vector itself is a mock in the subsequent experiments), the expression of enhanced green fluorescent protein (eGFP) was regulated by elongation factor-1α promoter (EF-1α). And in the recombinant expression vector pWPT-eGFP comprising a target nucleic acid sequence encoding CAR, the co-expression of eGFP and CAR is achieved by a ribosome jumping sequence 2A (abbreviated as F2A) from foot-and-mouth disease virus (FMDV).

The third aspect of the present invention includes a virus comprising the above-described vector. The viruses of the present invention include infectious viruses after packaging and also include viruses to be packaged that contain components necessary for the package of infectious viruses. Other viruses which can transfect T cells and their corresponding plasmid vectors known in the art can also be used in the present invention.

In one embodiment of the invention, the virus is a lentivirus comprising the pWPT-eGFP-F2A-CAR recombinant vector described above (i.e. containing scFv (EGFR)-CAR).

The fourth aspect of the present invention includes a transgenic T lymphocyte, which is transduced with a nucleic acid of the present invention or transduced with the above-mentioned recombinant plasmid containing the nucleic acid of the present invention or a viral system containing the plasmid. Conventional nucleic acid transduction methods in the art, including non-viral and viral transduction methods, can be used in the present invention. Non-viral transduction methods include electroporation and transposon methods. Recently, nucleofector nuclear transfection instrument developed by Amaxa can directly introduce foreign genes into nucleus to achieve highly efficient transduction of target genes. In addition, compared with conventional electroporation, the transduction efficiency of transposon system based on Sleeping Beauty system or PiggyBac transposon was significantly improved. The combination of nucleofector transfection instrument and SB Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10.], and high transduction efficiency and site-directed integration of target genes can be achieved by this method. In one embodiment of the invention, the transduction method of a T lymphocyte modified by a chimeric antigen receptor gene is a transduction method based on a virus such as a retrovirus or a lentivirus. The method has the advantages of high transduction efficiency and stable expression of exogenous gene, and the time for in vitro culturing T lymphocytes to clinical level can be shorten. The transduced nucleic acid is expressed on the surface of the transgenic T lymphocytes by transcription, translation. In vitro cytotoxicity assay performed on various cultured tumor cells demonstrated that the transgenic T lymphocytes expressing chimeric antigen receptors on the surface of the present invention have highly specific tumor cell killing effects (also known as cytotoxicity). Therefore, the nucleic acid encoding a chimeric antigen receptor protein of the present invention, a plasmid comprising the nucleic acid, a virus comprising the plasmid, and a transgenic T lymphocyte transfected with the nucleic acid, plasmid or virus described above can be effectively used in tumor immunotherapy.

MODES FOR CARRYING OUT THE INVENTION

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer, when the specification of the reagent company is specifically mentioned in the Examples.

Figure 1:
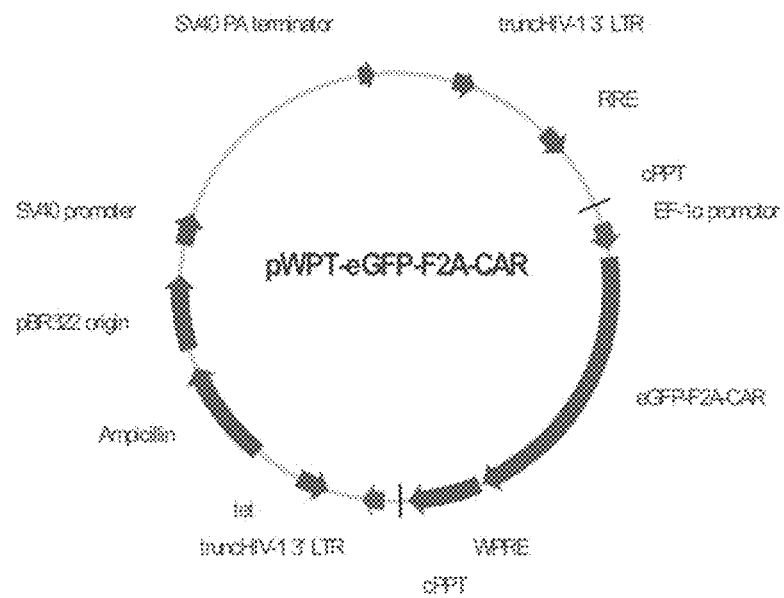
FIG. 1 shows, as an example, a schematic diagram of the structure of the lentiviral vector pWPT-eGFP-F2A-CAR of the present invention comprising CAR-encoding sequence.
Figure 2:
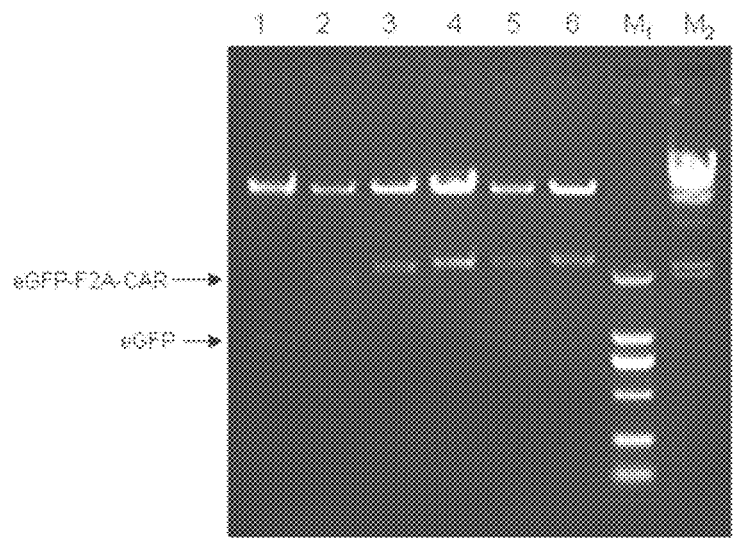
FIG. 2 shows, as an example, a schematic diagram of linkages between different domains of the CAR of the present invention contained in a lentiviral vector, in which eGFP and svFv (EGFR)-specific chimeric antigen receptors are linked by ribosome skipping sequence F2A.

Example 1. Construction of Lentiviral Plasmid Expressing the Chimeric Antigen Receptor of the Present Invention The connection order of each part in the exemplary chimeric antigen receptor of the invention is illustrated in following Table 1, which is also shown in FIG. 2.

TABLE 1

| chimeric antigen receptor | extracellular binding domain-transmembrane domain-intracellular signal domain 1-intracellular signal domain 2 | Description |
|---|---|---|
| 806-δ Z | scFv(EGFR)-CD8-CD3 δ zeta | Negative control |
| 806-Z | scFv(EGFR)-CD8-CD3 zeta | The 1st generation |
| 806-BBZ | scFv(EGFR)-CD8-CD137-CD3 zeta | The 2nd generation |
| 806-28Z | scFv(EGFR)-CD28-CD28-CD3 zeta | The 2nd generation |
| 806-28BBZ | scFv(EGFR)-CD28-CD28-CD137-CD3 zeta | The 3rd generation |

1. Amplification of Nucleic Acid Fragments (1) Amplification of scFv(EGFR) Sequence The sequence of scFv (EGFR) sequence was amplified by using single-stranded bifunctional antibody nucleotide 806/CD3 or hu7B3/CD3 constructed in our laboratory as template. The sequence of the template is shown in Chinese Patent Application 201210094008.x as SEQ ID NO: 10 and 11, respectively. And the primers used in amplification are:

upstream primer 5'-gacatcctgatgacccaatctccatcctc-3' (SEQ ID NO: 5) and downstream primer 5'-tgcagagacagtgaccagagtccccttgg-3' (SEQ ID NO: 6), used to amplify 806 scFv (EGFR);

and upstream primer 5'-gatattcagatgacccagagcccg-3' (SEQ ID NO: 7) and downstream primer 5'-gctgctcacggtcaccaggggtg-3' (SEQ ID NO: 8), used to amplify hu7B3 scFv (EGFR).

In both situations, the size of amplified target band was 720 bp. PCR amplification conditions were: pre-denaturation at 94° C. for 4 min; denaturation at 94° C. for 40 s; annealing at 58° C. for 40 s; extension at 68° C. for 40 s; 25 cycles; followed by a total extension at 68° C. for 10 min. PCR-amplified bands were confirmed by agarose gel electrophoresis to comply with the predicted fragment size.

The sequence of negative control scFv (CD19) was determined according to the sequence of FMC63-28Z (HM852952.1) from GenBank, and the sequence was obtained by Shanghai Ruijin Biotechnology Co. through whole-gene synthesis.

(2) Nucleic Acid Sequence of Other Parts of Chimeric Antigen Receptor

Other parts of the chimeric antigen receptor protein and the hinge region connecting these parts were amplified as follows: 1 ml Trizol (Invitrogen) was added into $1 \times 10^7$ healthy human peripheral blood mononuclear cells (provided by Shanghai Blood Center) for the lysis of cells; afterwards, total RNA was extracted by phenol-chloroform method; and cDNAs were prepared through reverse transcription by using ImProm-II™ Reverse Transcription Kit (Promaga). Above prepared cDNAs were used as templates in:

(a) amplification to obtain CD8a hinge region-transmembrane domain using upstream primer 5'-cactgtctctgcaaccacgacgccagcg-3' (SEQ ID NO: 9) and downstream primer 5'-ggtgataaccagtgacaggag-3' (SEQ ID NO: 10); and PCR amplification conditions were: pre-denaturation at 94° C. for 4 min; denaturation at 94° C. for 30 s; annealing at 58° C. for 30 s; extension at 68° C. for 30 s; 25 cycles; followed by a total extension at 68° C. for 10 min. The amplified product was confirmed by agarose gel electrophoresis to comply with the theoretical size, 198 bp.

(b) amplification to obtain CD8a hinge region-transmembrane domain-delta Z(δZ) by using upstream primer 5'-cactgtctctgcaaccacgacgccagcg-3' (SEQ ID NO: 11) and downstream primer 5'-gaggtcgacctacgcggggggcgtctgcgctcctgctgaacttcactctggtgataaccagtg-3' (SEQ ID NO: 12); and PCR amplification conditions were the same as above. The amplified product was confirmed by agarose gel electrophoresis to comply with the theoretical size, 234 bp.

(c) amplification to obtain CD28 transmembrane domain-Intracellular signal domain fragment by using upstream primer 5'-ttttgggtgctggtggtggttgg-3' (SEQ ID NO: 13) and downstream primer 5'-gctgaacttcactctggagcgataggctgcgaag-3' (SEQ ID NO: 14); and PCR amplification conditions were the same as above. The amplified product was confirmed by agarose gel electrophoresis to comply with the theoretical size, 465 bp.

(d) amplification to obtain CD137 Intracellular domain by using upstream primer 5'-aaacggggcagaaagaaactc-3' (SEQ ID NO: 15) and downstream primer 5'-cagttcacatcctccttc-3' (SEQ ID NO: 16); and PCR amplification conditions were the same as above. The amplified product was confirmed by agarose gel electrophoresis to comply with the theoretical size, 126 bp.

(e) amplification to obtain CD3 zeta signal domain by using upstream primer 5'-cactggttatcaccagagtgaagttcagcag-gagc-3' (SEQ ID NO: 17) and downstream primer 5'-cgag-gtcgacctagcgaggggggcagggcctgcatg-3' (SEQ ID NO: 18); and PCR amplification conditions were the same as above. The amplified product was confirmed by agarose gel electrophoresis to comply with the theoretical size, 339 bp.

2. Splicing of Nucleic Acid Fragments (a) upstream primer 5'-accacgacgccagcgccg-3' (SEQ ID NO: 19) and downstream primer 5'-cacccagaaaataataaag-3' (SEQ ID NO: 20) were used in splicing to obtain CD8a hinge region-CD28 transmembrane domain; and splicing conditions were: pre-denaturation of CD8a hinge region (50 ng)+CD28 transmembrane domain (50 ng) at 94° C. for 4 min; denaturation at 94° C. for 30 s; annealing at 60° C. for 30 s; extension at 68° C. for 30 s; 5 cycles; followed by a total extension at 68° C. for 10 min; DNA polymerase and upstream and downstream primers were supplemented, and afterwards PCR amplification was performed for 25 cycles; and PCR amplification conditions were: pre-denaturation at 94° C. for 4 min; denaturation at 94° C. for 30 s; annealing at 60° C. for 30 s; extension at 68° C. for 30 s; 25 cycles; followed by a total extension at 68° C. for 10 min. The amplified product was confirmed by agarose gel electrophoresis to comply with the theoretical size, 216 bp.

(b) upstream primer 5'-agagtgaagttcagcaggagcgcag-3' (SEQ ID NO:21) and downstream primer 5'-cgaggtcgac-ctagcgaggggggcagggcctgcatg-3' (SEQ ID NO:18) were used in splicing to obtain 4-1BB intracellular signal domain and CD3 zeta. i.e., BBZ; and splicing and PCR amplification conditions were the same as above. The amplified product was confirmed by agarose gel electrophoresis to comply with the theoretical size, 465 bp.

(c) upstream primer 5'-cactgtctctgcaaccacgacgccagcg-3' (SEQ ID NO: 22) and downstream primer 5'-cgaggtcgac-ctagcgaggggggcagggcctgcatg-3' (SEQ ID NO: 18) were used to splice equimolar of CD8a hinge region-transmembrane domain and CD3 zeta (about 50 ng), and CD8-CD3 zeta (i.e., CD8-Z) was obtained through PCR amplification; and splicing and PCR amplification conditions were the same as above. The amplified product was confirmed by agarose gel electrophoresis to comply with the theoretical size, 537 bp.

(d) upstream primer 5'-cactgtctctgcaaccacgacgccagcg-3' (SEQ ID NO: 23) and downstream primer 5'-cgaggtcgac-ctagcgaggggggcagggcctgcatg-3' (SEQ ID NO: 18) were used to splice CD8α hinge region-transmembrane domain and BBZ, and the target fragment, CD8-CD137-CD3 zeta (i.e., CD8-BBZ) was obtained through PCR amplification; and splicing and PCR amplification conditions were the same as above. The amplified product was confirmed by agarose gel electrophoresis to comply with the theoretical size, 663 bp.

(e) upstream primer 5'-accacgacgccagcgccg-3' (SEQ ID NO: 24) and downstream primer 5'-cgaggtcgacctagc-gaggggggcagggcctgcatg-3' (SEQ ID NO: 18) were used to splice CD8a hinge region-CD28 transmembrane domain and Z, and the target fragment, CD8 hinge region-CD28 transmembrane domain-28 Z intracellular domain was obtained through PCR amplification; and splicing and PCR amplification conditions were the same as above. The amplified product was confirmed by agarose gel electrophoresis to comply with the theoretical size, 678 bp.

(f) upstream primer 5'-accacgacgccagcgccg-3' (SEQ ID NO: 19) and downstream primer 5'-cgaggtcgacctagc-gaggggggcagggcctgcatg-3' (SEQ ID NO: 18) were used to splice CD8 hinge region, CD28 transmembrane domain-intracellular signal domain fragment obtained through PCR and BBZ, to obtain the target fragment, CD8 hinge region-CD28TM-28BBZ. The spliced and amplified product was confirmed by agarose gel electrophoresis to comply with the theoretical size, 804 bp.

(g) δZ, Z and 28BBZ nucleic acid fragments comprising hinge region and the transmembrane region respectively obtained by equimolar amplification were spliced with equimolar single-chain antibody nucleic acid sequence scFv806 or scFvCD19 (about 50 ng), and amplified by PCR, nucleic acid sequences encoding chimeric antibodies 806-δZ, 806-Z, 806-BBZ, 806-28Z and 806-28BBZ were obtained by splicing in the pattern shown in FIG. 2, and splicing and PCR amplification conditions were the same as above.

3. Construction of Plasmid Vector

The vector system used in this example belongs to the third-generation of self-inactivating lentiviral vector system. The system consists of three plasmids, namely packaging plasmid psPAX2 encoding Gag/Pol protein, Rev protein; envelope plasmid PMD2.G encoding VSV-G protein; and recombinant expression vector encoding target gene CAR based on blank vector pPWT-eGFP.

In the blank vector pPT-eGFP, the expression of enhanced green fluorescent protein (eGFP) was regulated by the promoter of elongation factor-1α (EF-1α). And in the recombinant expression vector encoding target gene CAR, the co-expression of eGFP and the target gene CAR was achieved by a ribosome jumping sequence 2A from foot-and-mouth disease virus (FMDV, F2A). F2A is a core sequence of 2A (or "self-cleaving polypeptide 2A") from foot-and-mouth disease virus, which possesses "self-cleaving" function of 2A and enables co-expression of upstream and downstream genes. 2A provides an effective and feasible strategy for constructing multicistronic vectors of gene therapy due to advantages of high cleaving efficiency, high balance of expression of upstream and downstream gene and short sequence. Especially in the immunotherapy of chimeric antigen receptor gene-modified T lymphocytes, the co-expression of target gene and GFP or eGFP is generally achieved by using such sequence, and the expression of CAR can be indirectly detected by detecting GFP or eGFP.

In this example, a lentiviral expression vector co-expressing eGFP and specific CAR linked by F2A was constructed, collectively named as pWPT-eGFP-F2A-CAR. Steps for splicing each part of eGFP-F2A-CAR are as follows:

Fragment of F2A (66 bp)-CD8a signal peptide (63 bp) and a small nucleic acid sequence (about 18 bp) fused with upstream eGFP and downstream CAR was obtained by primer splicing, the theoretical size of which was 165 bp. And the primers were:

```
                                      (SEQ ID NO: 25)
5'-attcaaagtctgtttcacgctactagctagtccg-3'

(SEQ ID NO: 26)
5'-gtgaaacagactttgaattttgaccttctgaagttggcaggagacgt tgagtccaac-3'

(SEQ ID NO: 27)
5'-agcggcaggagcaaggcggtcactggtaaggccatgggcccagggtt ggactcaacgtc-3'
```

-continued (SEQ ID NO: 28)
5'-ctcctgccgctggccttgctgctccacgccgccaggccggacatcct gatgacccaatc-3'

Splicing conditions for primer were: pre-denaturation at 94° C. for 4 min; denaturation at 94° C. for 20 s; annealing at 50° C. for 20 s; extension at 68° C. for 30 s; 25 cycles; followed by a total extension at 68° C. for 10 min. The amplified product was confirmed by agarose gel electrophoresis to comply with the theoretical size.

Upstream primer 5'-cttacgcgtcctagcgctaccggtcgccaccatg-gtgagcaagggcgaggag-3' (SEQ ID NO:29) and downstream primer 5'-gctactagctagtccggacttgtacagctcgtccatg-3' (SEQ ID NO:30) were used to amplify target gene eGFP, by using pWPT-eGFP blank vector as template. PCR amplification conditions were: pre-denaturation at 94° C. for 4 min; denaturation at 94° C. for 40 s; annealing at 56° C. for 40 s; extension at 68° C. for 40 s; 25 cycles; followed by a total extension at 68° C. for 10 min. The amplified product was confirmed by agarose gel electrophoresis to comply with the theoretical size, 735 bp.

Upstream primer 5'-cttacgcgtcctagcgctaccggtcgccaccatg-gtgagcaagggcgaggag-3' (SEQ ID NO: 29) and downstream primer 5'-gaggtcgacctacgcggggggcgtctgcgctcctgctgaact-tcactctggtgataaccagtg-3' (SEQ ID NO: 12) were used to splice equimolar of above obtained F2A-CD8α signal peptide fragment, eGFP and 806-δ Z (about 80 ng) to obtain eGFP-F2A-806-δ Z. And the splicing conditions were: pre-denaturation at 94° C. for 4 min; denaturation at 94° C. for 40 s; annealing at 62° C. for 40 s; extension at 68° C. for 140 s; 5 cycles; afterwards, DNA polymerase and upstream and downstream primers in a suitable volume were supplemented, and PCR amplification was performed for 25 cycles; and PCR amplification conditions were: pre-denaturation at 94° C. for 4 min; denaturation at 94° C. for 30 s; annealing at 62° C. for 40 s; extension at 68° C. for 140 s. The amplified product was confirmed by agarose gel electrophoresis to comply with the theoretical size, 1861 bp.

Figure 3:
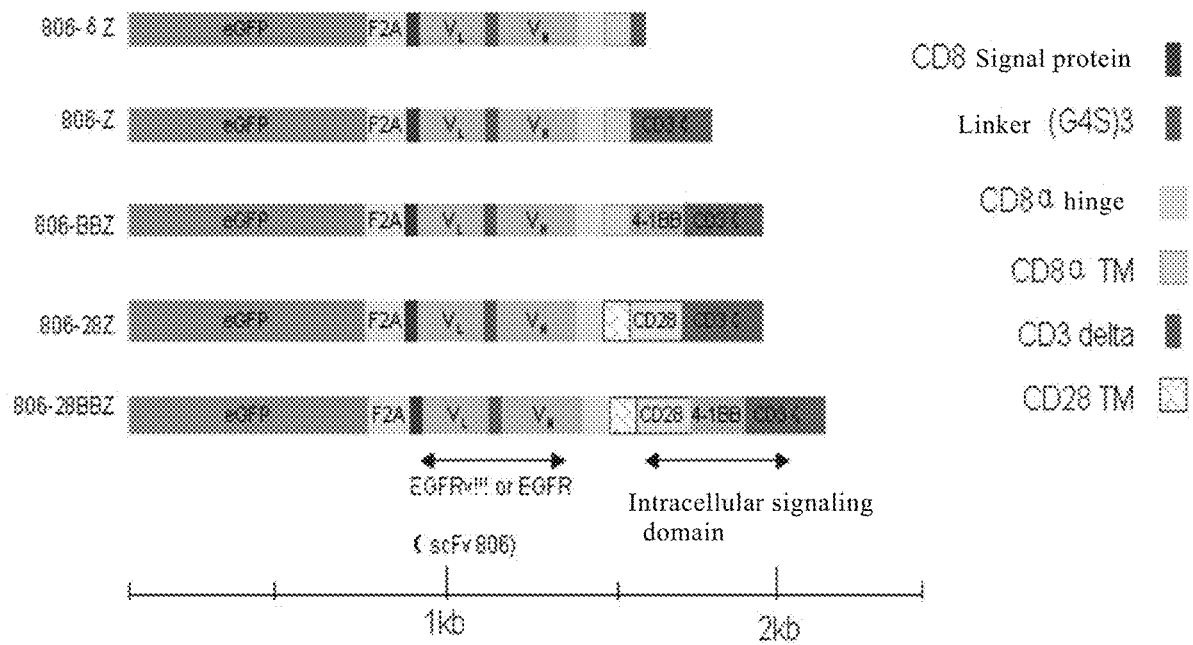
FIG. 3 shows a nucleic acid electrophoresis map of the lentiviral plasmid of Example 1 identified by double digestion of MluI and SalI. Wherein M1 is a DS2000 molecular weight marker (Guangzhou Dongsheng Biotechnology Co., Ltd.); and M2 is a Hind III marker (Guangzhou Dongsheng Biotechnology Co., Ltd.). Lanes 1-6 are 1: pWPT-eGFP; 2: pWPT-eGFP-F2A-806-δ Z; 3: pWPT-eGFP-F2A-806-Z; 4: pWPT-eGFP-F2A-806-BBZ; 5: pWPT-eGFP-F2A-806-28Z; 6: pWPT-eGFP-F2A-806-28BBZ, respectively.

Upstream primer 5'-cttacgcgtcctagcgctaccggtcgccaccatg-gtgagcaagggcgaggag-3' (SEQ ID NO: 29) and downstream primer 5'-gaggtcgacctagcgaggggggcagggcctgcatgtgaag-3' (SEQ ID NO: 18) were used to splice equimolar of above obtained F2A and CD8a signal peptide fragments, eGFP and 806-Z, 806-BBZ, CD19-BBZ, 806-28Z as well as 806-28BBZ (about 80 ng) respectively. And the splicing conditions were: pre-denaturation at 94° C. for 4 min; denaturation at 94° C. for 40 s; annealing at 62° C. for 40 s; extension at 68° C. for 140 s; 5 cycles; afterwards, DNA polymerase and upstream and downstream primers in a suitable volume were supplemented, and PCR amplification was performed for 25 cycles; and PCR amplification conditions were: pre-denaturation at 94° C. for 4 min; denaturation at 94° C. for 40 s; annealing at 62° C. for 40 s; extension at 68° C. for 140 s.

eGFP-F2A-806-Z, eGFP-F2A-806-BBZ, eGFP-F2A-806-28Z and eGFP-F2A-806-28BB Z were obtained, the theoretical size of which were 2164 bp, 2290 bp, 2305 bp, 2431 bp respectively, and the amplified products were confirmed by agarose gel electrophoresis to comply with the theoretical sizes, wherein MluI and SalI cleavage sites were introduced upstream and downstream of the open reading frame. The above obtained target gene eGFP-F2A-CAR was digested with MluI and SalI, and ligated into pWPT vector digested with the same enzymes. The constructed lentiviral vector expressing each chimeric antigen receptor was digested by MluI and SalI (FIG. 3) and the sequence was determined as correct for lentivirus packaging.

As described previously, eGFP-F2A-CAR was transcribed into mRNA, but translated into two proteins, eGFP and anti-EGFR287-302 chimeric antigen receptor. Under the action of CD8α signal peptide, anti-EGFR287-302 chimeric antigen receptor will be located on cell membrane.

4. 293Tcells were Transfected by Plasmids for Packaging Lentivirus 293T cells (ATCC: CRL-11268) which were cultured to $6^{th}$-$10^{th}$ generation were inoculated into a 10 cm dish at a density of $6 \times 10^6$, and cultured overnight at 37° C., 5% $CO_2$ for transfection. The medium was DMEM (PAA) containing 10% fetal bovine serum (PAA). The next day, the medium was replaced with serum-free DMEM at about 2 hours before transfection.

The procedure for transfection was as follows 4.1 20 μg of blank plasmid pWPT-GFP (mock control) or 20 μg of target gene plasmid pWPT-eGFP-F2A-CAR were mixed with 15 μg of packaging plasmid PAX2 and 6 μg of envelope plasmid pMD2.G into 500 μL of MillQ water, 4.2 62 μL of 2.5 M $CaCl_2$ (Sigma) was added dropwise and mixed at 1200 rpm/min vortex, 4.3 Finally, 500 μL of 2×HeBS (280 mM NaCl, 10 mM KCl, 1.5 mM Na2HPO4.2H2O, 12 mM glucose, 50 mM Hepes, Sigma, pH 7.0, 0.22 μM) was added dropwise and was mixed at 1200 rpm/min vortex for 10 seconds, 4.4 immediately added dropwise to the Petri dish, gently shaken, cultured at 37° C., 5% $CO_2$ for 4~6 h, and replaced with DMEM containing 10% fetal calf serum.

Transfection efficiency was observed on the next day of transfection (i.e., the proportion of cells with green fluorescence), and ~80% of positive transfection efficiency was deemed as successful transfection. After 48 h or 72 h of transfection, virus was collected by filtration using a 0.45 μm filter (Millipore) and centrifuged at 28,000 rpm for 2 hours at 4° C. using Beckman Optima L-100XP ultracentrifuge. The supernatant was discarded, and the obtained pellet was resuspended in Quantum 007 culture liquid (PAA) at ⅒~1/50 volume of stock solution, and stored at −80° C. at 100 μL/tube for virus titration or infection of T lymphocytes.

5. Determination of Titer of Lentivirus with Packaged Mock or GFP-F2A-CAR

On the first day, 293T cells were inoculated at $1 \times 10^5$/mL into 96-well culture plate, 100 μL/well, and cultured at 37° C., 5% $CO_2$, and the culture medium was DMEM containing 10% fetal bovine serum. The next day, 50 μL/well of culture supernatant was discarded, 50 μL/well of the fresh culture medium was added, polybrene at a final concentration of 6 μg/mL was contained, and cells were cultured for 30 minutes at 37° C. and 5% $CO_2$. 10 μL/well of virus stock solution or 1 μL/well of virus concentrate was added at 5-fold dilution, and 4 gradients, in duplicate, and cells were cultured at 37° C., 5% $CO_2$. 48 h after infection, eGFP was detected by flow cytometry, the number of cells at the positive rate of 5 to 20% was appropriate, and titer (U/mL) was calculated according to positive rate×dilution multiple×100×104. The titer of packaged virus through calcium phosphate transfection method was about 0.5~$2 \times 10^6$ U/mL, and after concentration, the titer of virus was detected as about $2 \times 10^7$ U/mL.

Example 2. Infection of CD8+ T Lymphocytes by Recombinant Lentivirus

Human peripheral blood mononuclear cells were obtained from healthy human peripheral blood (provided by Shanghai Blood Center) by density gradient centrifugation. CD8+ T lymphocytes were obtained from peripheral blood mononuclear cells through negative sorting method by using CD8$^+$ T lymphocyte beads (Stem Cell Technologies). Sorted CD8$^+$ T lymphocytes were tested for the purity of CD8$^+$ T lymphocytes through flow Cytometry, and if the positive rate of CD8$^+$ T lymphocyte is ≥95%, it is appropriate for the next operation. Quantum 007 lymphocyte culture medium (PAA) was added at a density of about 1×10$^6$/mL for culture, magnetic beads coated with anti-CD3 and CD28 antibodies (Invitrogen) were added at cell: magnetic bead of 1:1, and cells were stimulated and cultured for 24 h with recombinant human IL-2 (Shanghai Huaxin Biotechnology Co., Ltd.) at a final concentration of 100 U/mL. And then, CD8$^+$ T lymphocytes were infected by the above recombinant lentivirus at MOI ≈5. Infected cells were passaged every other day at a density of 5×10$^5$/mL and recombinant human IL-2 was supplemented in the lymphocyte culture medium at a final concentration of 100 U/mL.

Figure 4:
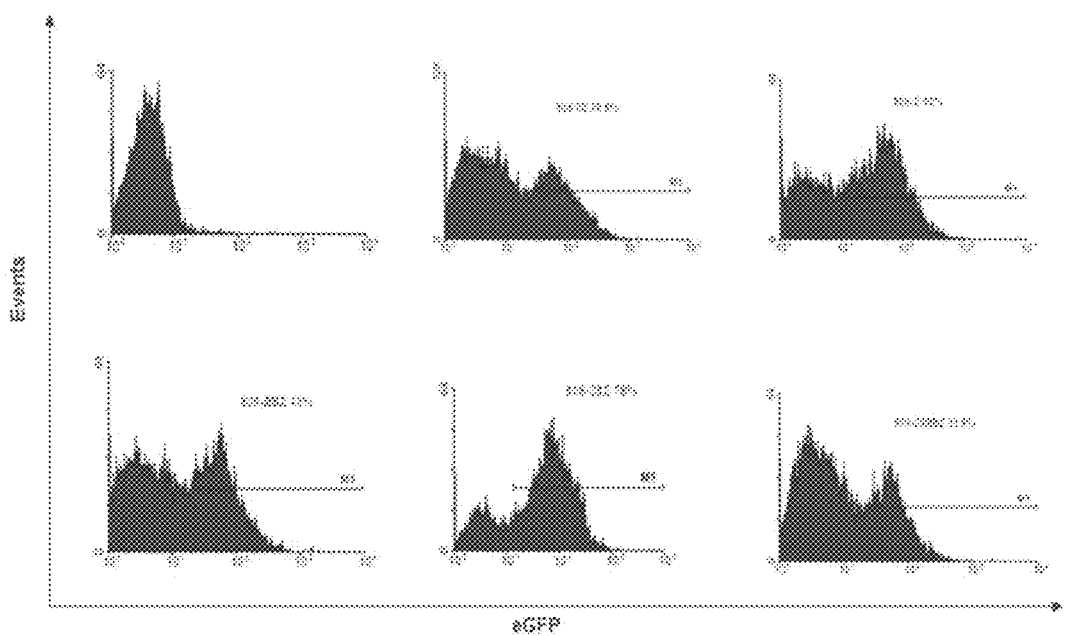
FIG. 4 shows the results of flow cytometry of eGFP expressed in $CD8^+$ T lymphocytes infected with the virus of Example 2 of the present invention.

At the 7$^{th}$ day of culture, infected CD8$^+$ T lymphocytes were detected by flow cytometry for the expression of different chimeric antigen receptors, detected eGFP-positive cells were deemed as positive cells expressing chimeric antigen receptors due to the co-expression of eGFP and CAR (FIG. 4). Positive ratio of CD8$^+$ T lymphocytes infected by the virus and expressing different chimeric antigen receptors are shown in the following table, with uninfected T lymphocytes as negative control. The positive rate demonstrates that certain positive rate of CAR$^+$ T lymphocytes can be obtained by lentivirus infection.

TABLE 2

| CD8$^+$ T lymphocytes transfected with the following CARs | eGFP positive rate of CD8$^+$ T lymphocyte |
|---|---|
| 806-δ Z | 38.8% |
| 806-Z | 62% |
| 806-BBZ | 45% |
| 806-28Z | 78% |
| 806-28BBZ | 33.8% |

Figure 5:
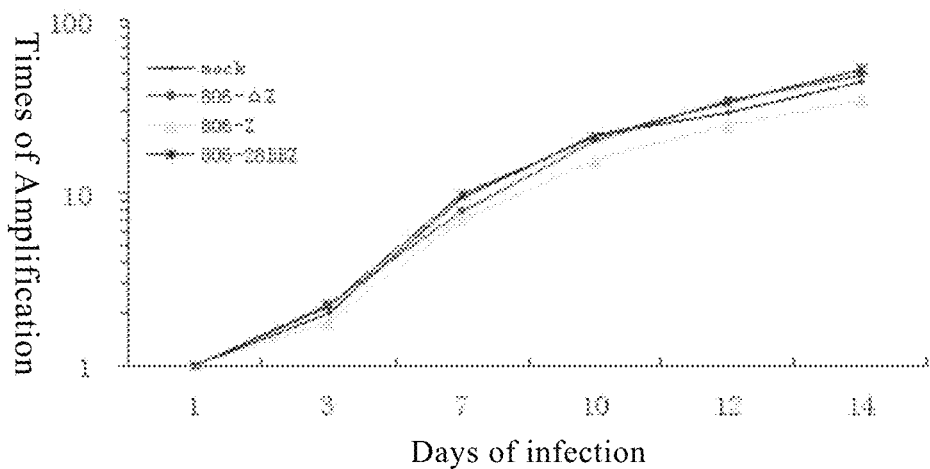
FIG. 5 shows the in vitro growth of $CD8^+$ T lymphocytes expressing different chimeric antigen receptors ($CAR^+$) according to Example 2 of the present invention.

After infected by viruses packaging different chimeric antigen receptors, CD8$^+$ T lymphocytes were subcultured at a cell density of 5×10$^5$/ml every other day and counted. And IL-2 (final concentration of 100 U/ml) was supplemented into cell culture fluid for subculture. On the 14$^{th}$ day of culture, about 35~55 folds of amplification can be observed (see FIG. 5), indicating that CD8$^+$ T lymphocytes expressing different chimeric antigen receptors could be amplified in vitro in a certain quantity, thereby guaranteeing subsequent in vitro toxicity test and in vivo test.

Example 3. Detection of Exposure of EGFR287-302 Epitope in Epithelial-Derived Tumor Cell Lines Exposure of EGFR287-302 epitope on several epithelial-derived tumor cells was examined by flow cytometry using a fluorescence activated cell sorter (FACSCalibur, Becton Dickinson). Used materials include:

(1) Monoclonal antibody CH12, which was constructed by our laboratory and can recognize this site (see CN 101602808B, Examples 1-4 for the construction method) was used as primary antibody (final concentration 20 μg/ml, 100 μL/sample), (2) FITC-labeled goat anti-human IgG was used as secondary antibody (AOGMA).

The detection method for the exposure of epitope is as follows:

1. Tumor cells as shown in Table 3 in logarithmic growth phase were inoculated into 6 cm dishes at a cell density of about 90%, and incubated overnight at 37° C.
2. The cells were digested with 10 mM EDTA, collected by centrifugation at 200 g×5 min, resuspended in phosphate buffer (1% NBS/PBS) containing 1% fetal bovine serum at a concentration of ~1×10$^7$/mL and added to a tube for flow cytometry at 100 μl/tube.
3. The cells were centrifuged at 200 g×5 min, and the supernatant was discard.
4. In the experimental group, CH12 was added, while in the control group, irrelevant antibody was added as the negative control. In another control group, PBS without antibody was added as blank control. The final concentration of each antibody was 20 μg/ml, and 100 ul was added into each tube, and placed into an ice bath for 45 minutes.
5. 2 ml of 1% NBS/PBS was added into each tube, and centrifuged at 200 g×5 min for two times.
6. The supernatant was discarded, and 1:50 dilution of FITC-labeled goat anti-human IgG was added and placed into an ice bath for 45 minutes.
7. 2 ml of 1% NBS/PBS was added into each tube, and centrifuged at 200 g×5 min for two times.
8. The supernatant was discarded, and cells were resuspended in 300 ul of 1% NBS PBS and detected by flow cytometry.
9. Data were analyzed using WinMDI 2.9, a data analysis software of flow cytometry.

Figure 6:
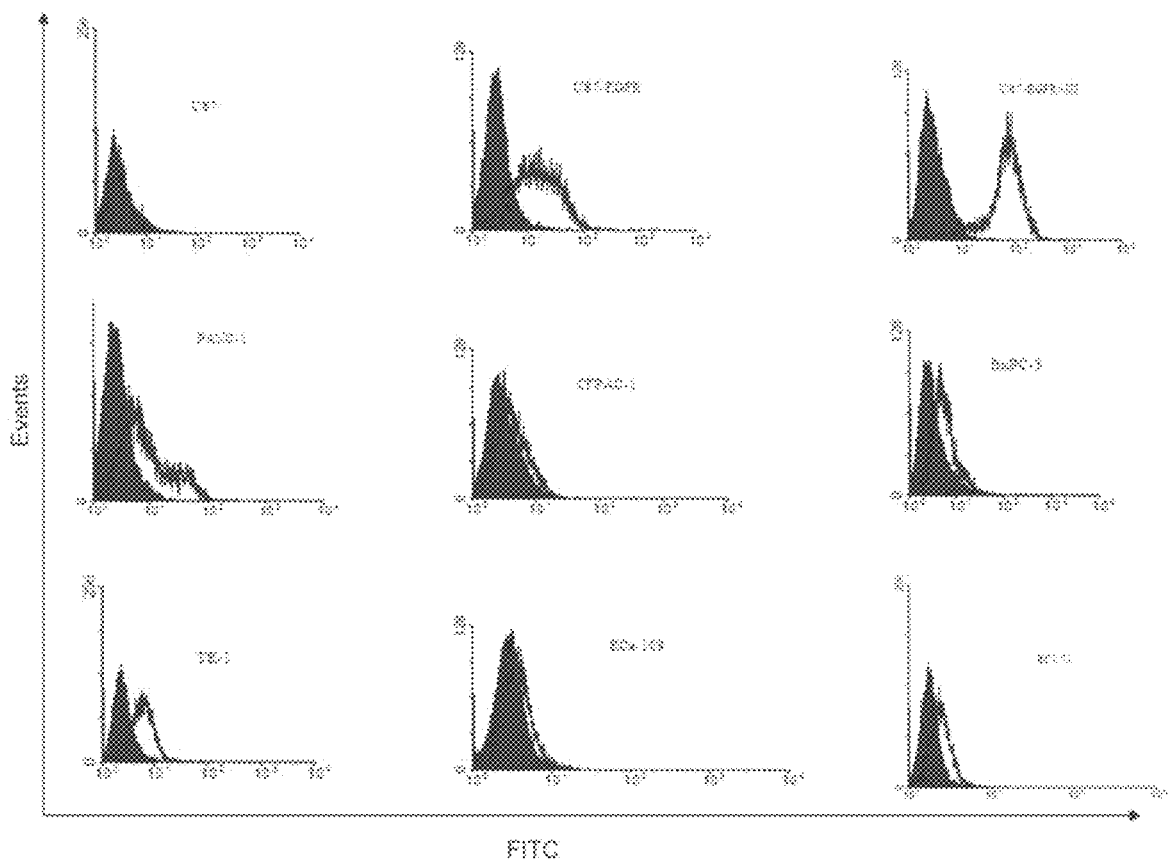
FIG. 6 shows the results of flow cytometry of the expression of EGFR287-302 epitope on the surface of various tumor cell lines used in Example 3 of the present invention.

Results are shown in FIG. 6, wherein EGFR287-302 epitope was not detected in glioma cell line U87, while in U87-EGFR over-expressing exogenous EGFR (constructed and preserved in our laboratory, and the construction method is based on Wang H., et al., Identification of an Exon 4-Deletion Variant of Epidermal Growth Factor Receptor with Increased Metastasis-Promoting Capacity. Neoplasia, 2011, 13, 461-471) and U87-EGFRvIII with over-expressing EGFRvIII (constructed and preserved in our laboratory, and the construction method is based on WO/2011/035465), EGFR287-302 epitope was detected. Additionally, exposure of EGFR287-302 epitope can be detected in three pancreatic cancer cell lines PANC-I, CFPAC-I and BxPC-3.

TABLE 3

| Name of cell | Source | Characteristic |
|---|---|---|
| U87 | ATCC HTB-14 | Low-expression of EGFR |
| U87-EGFRvIII | constructed and preserved in our laboratory | Over-expression of EGFRvIII |
| U87-EGFR | constructed and preserved in our laboratory | Over-expression of EGFR |
| PANC-1 | ATCC CRL-1469 | Over-expression of EGFR |
| CFPAC-1 | ATCC CRL-1918 | Over-expression of EGFR |
| BxPC-3 | ATCC CRL-1687 | Over-expression of EGFR |

Example 4. In Vitro Experiment on Toxic Efficacy of Cells Expressing Chimeric Antigen Receptor Materials used in the in vitro toxicity experiment are as follows:

Target cells were 6 types of cells as shown in the above table. Effector cells were positive cells which were in vitro cultured for 12 days and detected as expressing chimeric antigen receptor by FASC, which were marked as chimeric antigen receptor positive (CAR$^+$) CD8$^+$ T lymphocytes.

The effector target rates were 3:1, 1:1 and 1:3 or 5:1, 2.5:1 and 1:1, respectively. The number of target cells was 10000/well, and the number of effector cells corresponded to different effector target rates. In each group, four replicates were set, and the average of the four replicate wells was taken. Detection time was 18 h or 20 h.

Wherein each experiment group and each control group were as follows:

each experiment group: each target+CD8+ T lymphocytes expressing different chimeric antigen receptors, Control group 1: maximum release of LDH from target cells, Control group 2: spontaneous release of LDH from target cells, Control group 3: spontaneous release of LDH from effector cells.

Detection method: CytoTox 96 non-radioactive cytotoxicity assay kit (Promega) was used to perform the method. The method is a detection method based on colorimetric method, which can replace 51Cr release method. CytoTox 96® assay quantitatively measures lactate dehydrogenase (LDH). LDH is a stable cytoplasmic enzyme which is released during cell lysis and is released in the same manner as 51Cr released in radioactivity analysis. The culture supernatant, in which LDH is released, can be detected through enzymatic reaction of 30-minute conjugation, in which LDH converts a tetrazolium salt (INT) into a red formazan. The amount of formed red product is directly proportional to the number of lysed cells. Details can be found in CytoTox 96 non-radioactive cytotoxicity test kit instructions.

The formula for calculating cytotoxicity was:

$$\text{Cytotoxicity \%} = \frac{\text{Experiment group-control group 2-control group 3}}{\text{Control group 1-control group 2}} \times 100\%$$

Experiment results demonstrate that:

The CD8+ T lymphocytes expressing scFv (EGFR)-806-Z CAR$^P$ and CD8+ T lymphocytes expressing 806-28BBZ CAR+ of the present invention showed very significant cytotoxicity against tumor cells U87-EGFRvIII, which were 55.5% and 85%, respectively.

Additionally, the cytotoxicity of CD8+ T lymphocytes of the present invention described above is highly tumor-specific, since the CD8+ T lymphocytes showed high cytotoxicity against tumor cells U87-EGFRvIII with the exposure of EGFR287-302 epitope, while showed low cytotoxicity against tumor cells U87 without the exposure of EGFR287-302 epitope, less than 2% in both cases. At the same time, the mock-transfected T cells used as blank control of the evidence of experiment reliability and chimeric antigen receptor 806-δZ transgenic T cells, as a negative control for evaluating effects of effector molecules in primitive T cells, showed similar low cytotoxicity against U87 and U87-EGFRvIII. The above experiment was performed at a effector to target rate of 5:1 and an action time of 20 h.

TABLE 4

| | Cytotoxicity against target cells % | |
|---|---|---|
| CAR+ T cells | U87 | U87-EGFRvIII |
| 806-Z CAR+ | <2 | 56 |
| 806-28BBZ CAR+ | <2 | 85 |
| 806-δ Z CAR+ | <2 | 5 |
| mock CAR+ | <2 | 8 |

In addition, under different effector to target rates, the cytotoxicity of CD8+ T lymphocytes expressing scFv (EGFR)-806-Z CAR+ and CD8+ T lymphocytes expressing 806-28BBZ CAR+ of the present invention against tumor cells U87-EGFR and U87-EGFRvIII as well as pancreatic cancer cell lines PANC-1, CFPAC-1 and BxPC-3 exhibited dependence on effector to target rate gradient. As shown in the following table, the higher the effector to target rate, the higher the cytotoxicity.

| | Cytotoxicity % | | | | | | | | |
|---|---|---|---|---|---|---|---|---|---|
| | 806-28BBZ at different effector to target rates | | | 806-Z at different effector to target rates | | | CD19-BBZ at different effector to target rates | | |
| | 3:1 | 1:1 | 1:3 | 3:1 | 1:1 | 1:3 | 3:1 | 1:1 | 1:3 |
| U87 | -2 | -14 | -25 | n/a | n/a | n/a | n/a | n/a | n/a |
| U87-EGFR | 98 | 49 | 29 | n/a | n/a | n/a | n/a | n/a | n/a |
| U87-EGFRvIII | 81 | 41 | 13 | n/a | n/a | n/a | n/a | n/a | n/a |
| PANC-1 | 65 | 28 | 13 | 60 | 34 | 18 | -7 | -11 | -8 |
| CFPAC-1 | 40 | 22 | 9 | 43 | 35 | 12 | 8 | 8 | 6 |
| BxPC-3 | 70 | 49 | 24 | 44 | 24 | 14 | 7 | 10 | 8 |

When the effector to target rate was 3:1, the cytotoxicity of CD8+ T lymphocytes expressing 806-28BBZ CAR+ against U87-EGFR was up to 98%, the cytotoxicity against U87-EGFRvIII was up to 81%, and the cytotoxicity against pancreatic cancer cell lines PANC-1, CFPAC-1 and BxPC-3 was 65%, 40% and 70% respectively.

However, the cytotoxicity of CD8+ T lymphocytes expressing chimeric antigen receptor CD19-BBZ CAR+, as a negative control for evaluating effects of non-specific scFv in chimeric antigen receptor, against the above pancreatic cancer cell lines is lower than 10%, and no dependence on effector to target rate gradient was observed.

The invention claimed is:

1. A nucleic acid encoding a chimeric antigen receptor protein expressed on a surface of a human T lymphocyte, wherein the chimeric antigen receptor protein comprises an extracellular binding domain, a transmembrane domain and an intracellular signal domain, wherein the extracellular binding domain comprises a single chain antibody having at least 95% sequence homology to any one of SEQ 31-34 in the framework region, and wherein the extracellular binding domain binds to the $287^{th}$-$302^{nd}$ amino acid epitopes of human epidermal growth factor receptor (EGFR).

2. The nucleic acid of claim 1, wherein the intracellular signal domain is selected from the sequence of intracellular signal domain of CD3ζ, FcεRIγ, CD28, CD137, CD134, or combinations thereof.

3. The nucleic acid of claim 2, wherein the chimeric antigen receptor protein is the following chimeric antigen receptor protein comprising any one of:
   extracellular domain scFv(EGFR)-transmembrane domain CD8-intracellular domain CD3ζ,
   extracellular domain scFv(EGFR)-transmembrane domain CD8-intracellular domain CD137-intracellular domain CD3ζ,
   extracellular domain scFv(EGFR)-transmembrane domain CD28-intracellular domain CD28-intracellular domain CD3ζ,
   extracellular domain scFv(EGFR)-transmembrane domain CD28-intracellular domain CD28-intracellular domain CD137-intracellular domain CD3ζ,
   or combinations thereof.

4. The nucleic acid of claim 1, wherein the nucleic acid comprises SEQ ID NO:32.

5. The nucleic acid of claim 1, wherein the nucleic acid has a sequence of SEQ ID NO: 2.

6. The nucleic acid of claim 1, wherein the nucleic acid comprises SEQ ID NO:31.

7. The nucleic acid of claim 1, wherein the nucleic acid comprises SEQ ID NO:33.

8. The nucleic acid of claim 1, wherein the nucleic acid comprises SEQ ID NO:34.

9. The nucleic acid of claim 1, wherein the nucleic acid has a sequence of SEQ ID NO: 1.

10. The nucleic acid of claim 1, wherein the nucleic acid has a sequence of SEQ ID NO: 3.

11. The nucleic acid of claim 1, wherein the nucleic acid has a sequence of SEQ ID NO: 4.

12. The nucleic acid of claim 1, wherein the transmembrane domain comprises a hinge region, wherein the hinge region links the transmembrane domain to the extracellular binding domain.

13. The nucleic acid of claim 12, wherein the transmembrane domain comprises the sequence of transmembrane domain and hinge region of CD8 or CD28.

14. A vector comprising a nucleic acid of encoding a chimeric antigen receptor protein expressed on a surface of a human T lymphocyte, wherein the chimeric antigen receptor protein comprises an extracellular binding domain, a transmembrane domain and an intracellular signal domain, and wherein the extracellular binding domain comprises a single-chain antibody scFv having at least 95% sequence homology to any one of SEQ 31-34 in the framework region, and wherein the extracellular binding domain binds to the 287th-302nd amino acid epitopes of human epidermal growth factor receptor (EGFR).

15. The vector of claim 14, wherein the vector is derived from a lentiviral plasmid vector pPWT-eGFP.

16. A virus comprising a nucleic acid encoding a chimeric antigen receptor protein expressed on a surface of a human T lymphocyte, wherein the chimeric antigen receptor protein comprises an extracellular binding domain, a transmembrane domain and an intracellular signal domain, and wherein the extracellular binding domain comprises a single-chain antibody scFv having at least 95% sequence homology to any one of SEQ 31-34 in the framework region, and wherein the extracellular binding domain binds to the 287th-302nd amino acid epitopes of human epidermal growth factor receptor (EGFR).

17. A transgenic T lymphocyte, which is transduced with a nucleic acid of encoding a chimeric antigen receptor protein expressed on a surface of a human T lymphocyte, wherein the chimeric antigen receptor protein comprises an extracellular binding domain, a transmembrane domain and an intracellular signal domain, and wherein the extracellular binding domain comprises a single-chain antibody scFv having at least 95% sequence homology any one of SEQ 31-34 in the framework region, and wherein the extracellular binding domain binds to the 287th-302nd amino acid epitopes of human epidermal growth factor receptor (EGFR).

18. A transgenic T lymphocyte, wherein a chimeric antigen receptor is expressed on the surface of the T lymphocyte and the chimeric antigen receptor is encoded by a nucleic acid of encoding a chimeric antigen receptor protein expressed on a surface of a human T lymphocyte, wherein the chimeric antigen receptor protein comprises an extracellular binding domain, a transmembrane domain and an intracellular signal domain, and wherein the extracellular binding domain comprises a single-chain antibody scFv having at least 95% sequence homology any one of SEQ 31-34 in the framework region, and wherein the extracellular binding domain binds to the 287th-302nd amino acid epitopes of human epidermal growth factor receptor (EGFR).

* * * * *